United States Patent
Brickley

(10) Patent No.: US 6,924,495 B1
(45) Date of Patent: Aug. 2, 2005

(54) HEAT CONTROLLED ULTRAVIOLET LIGHT APPARATUS AND METHODS OF SANITIZING OBJECTS USING SAID APPARATUS

(76) Inventor: James Lawrence Brickley, 100 Ward Rd., Anaconda, MT (US) 59711

( * ) Notice: Subject to any disclaimer, the term of this patent is extended or adjusted under 35 U.S.C. 154(b) by 12 days.

(21) Appl. No.: 10/778,637

(22) Filed: Feb. 13, 2004

(51) Int. Cl.$^7$ .............................. H01J 61/30; H01J 61/32
(52) U.S. Cl. .............................. 250/504 R; 250/453.11; 250/454.11; 250/455.11; 250/493.1; 250/494.1; 313/10; 313/11; 313/13; 313/15; 313/17; 313/25; 313/26; 313/33; 313/45
(58) Field of Search .................. 250/504 R, 453.11, 250/454.11, 455.11, 493.1, 494.1; 313/10, 11, 13, 15, 17, 25, 26, 33, 45, 112, 634; 34/275, 276, 549, 553, 523, 643, 278; 502/5

(56) References Cited

U.S. PATENT DOCUMENTS

| | | | |
|---|---|---|---|
| 3,571,939 A | | 3/1971 | Paul .............................. 34/1 |
| 4,074,163 A | * | 2/1978 | van der Leeuw ............ 313/13 |
| 4,150,280 A | * | 4/1979 | Hurko ..................... 219/455.12 |
| 4,179,616 A | * | 12/1979 | Coviello et al. .......... 422/186.3 |
| 4,237,368 A | * | 12/1980 | Welch ..................... 219/448.17 |
| 4,298,005 A | * | 11/1981 | Mutzhas ..................... 607/94 |
| 4,877,997 A | * | 10/1989 | Fein .......................... 313/634 |
| 4,916,352 A | * | 4/1990 | Haim et al. .................. 313/25 |
| 4,949,004 A | * | 8/1990 | Yamazaki et al. ............ 313/35 |
| 4,955,208 A | | 9/1990 | Kawashima et al. ......... 62/264 |
| 4,965,484 A | * | 10/1990 | Fein ........................... 313/15 |
| 5,223,290 A | * | 6/1993 | Alden ........................ 426/243 |
| 5,245,246 A | * | 9/1993 | Boland et al. ............... 313/15 |
| 5,505,912 A | * | 4/1996 | Hallett ..................... 422/186.3 |
| 5,677,190 A | * | 10/1997 | Melanson et al. .......... 436/146 |
| 5,864,209 A | | 1/1999 | Clark ........................ 313/622 |
| 5,902,552 A | | 5/1999 | Brickley ..................... 422/121 |
| 5,968,455 A | | 10/1999 | Brickley ..................... 422/121 |
| 6,058,718 A | * | 5/2000 | Forsberg et al. ............. 62/125 |
| 6,114,809 A | * | 9/2000 | Winsor ....................... 315/50 |
| 6,193,894 B1 | | 2/2001 | Hollander ................. 210/748 |
| 6,395,240 B1 | * | 5/2002 | Fujii et al. ............... 422/186.3 |
| 6,614,039 B2 | | 9/2003 | Hollander .................. 250/504 |
| 2001/0006162 A1 | | 7/2001 | Hollander ................. 210/748 |
| 2001/0050218 A1 | * | 12/2001 | Tabatabaie-Raissi et al. ..................... 204/157.15 |
| 2002/0060529 A1 | | 5/2002 | Wood et al. ............... 315/291 |
| 2003/0001112 A1 | | 1/2003 | Hollander .................. 250/504 |
| 2003/0038247 A1 | | 2/2003 | Schweitzer et al. .... 250/455.11 |

FOREIGN PATENT DOCUMENTS

| | | | | |
|---|---|---|---|---|
| JP | 401086440 A | | 3/1989 | |
| JP | 2004077002 A | * | 3/2004 | ............ F24F/1/00 |

* cited by examiner

Primary Examiner—John R. Lee
Assistant Examiner—Bernard E. Souw
(74) Attorney, Agent, or Firm—Sheridan Ross P.C.

(57) ABSTRACT

A heat controlled ultraviolet light apparatus includes a source of ultraviolet light, a cover, and a heating or cooling element that heats/cools the space or gap between the ultraviolet light source and the cover. Accordingly, the ultraviolet light source may be maintained at an optimal temperature thereby maximizing the efficiency of the ultraviolet light source in producing ultraviolet radiation. The apparatus may further include a temperature sensor and a control circuit to automatically control production of heat/cooling by the element based upon the ambient temperatures experienced by the ultraviolet light source during use. Methods are also provided for sanitizing heating and cooling coils of various devices such as an HVAC system, and cooling systems such as a refrigeration unit and an evaporative cooler.

32 Claims, 2 Drawing Sheets

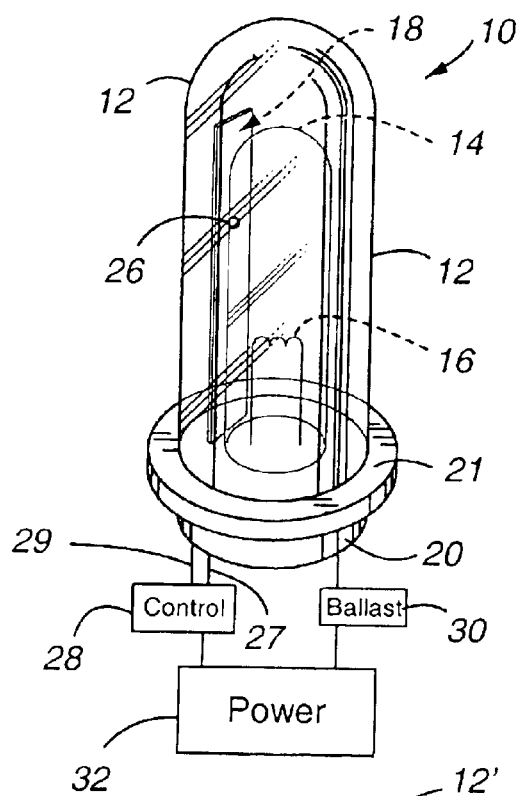
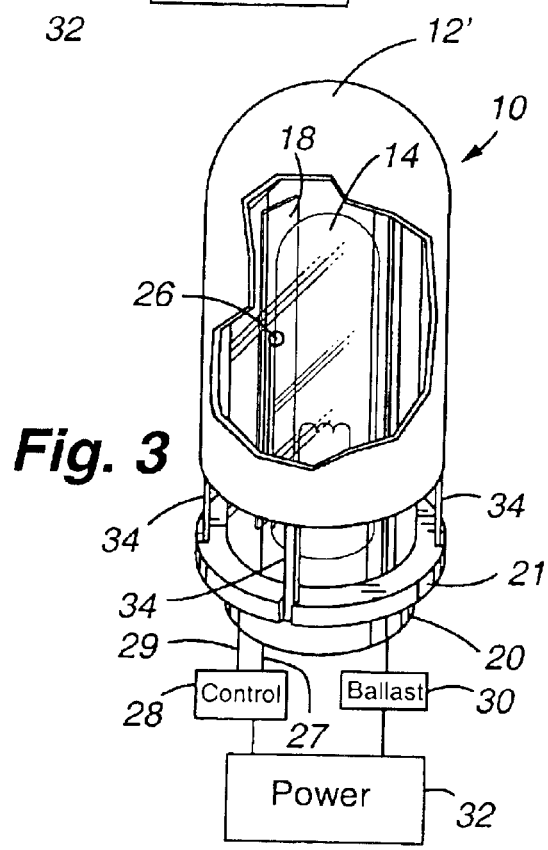
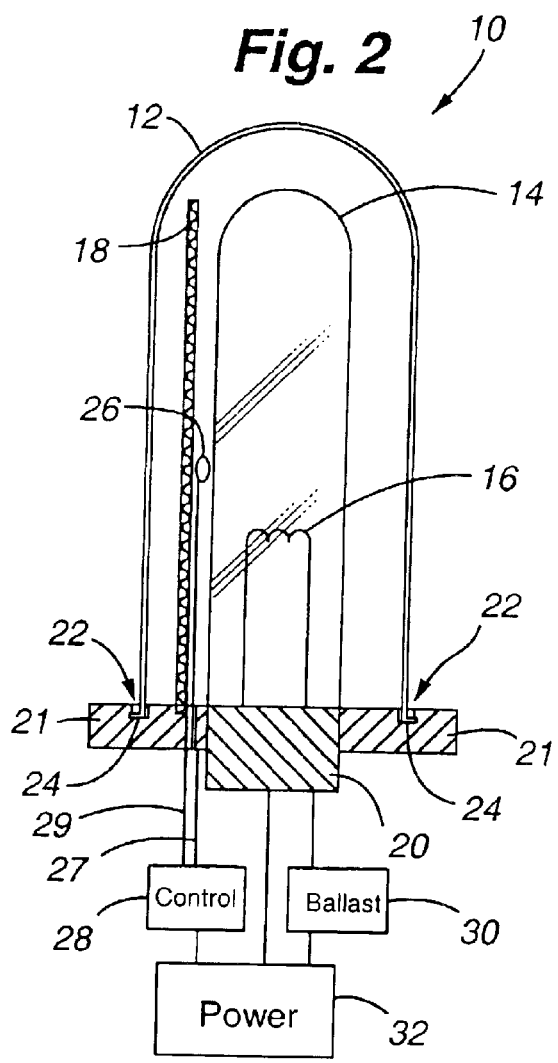

HEAT CONTROLLED ULTRAVIOLET LIGHT APPARATUS AND METHODS OF SANITIZING OBJECTS USING SAID APPARATUS

TECHNICAL FIELD

The present invention relates generally to methods and apparatuses for disinfecting objects utilizing an ultraviolet light source, and more particularly, to an ultraviolet light source that is maintained at a desired temperature range by heating or cooling, as necessary, thereby maximizing the efficiency of the ultraviolet light source in producing ultraviolet rays.

BACKGROUND OF THE INVENTION

An ultraviolet light source is a well known means for sanitizing and disinfecting many targeted objects to include fluids. When administered at the desired frequencies, durations, and intensities, ultraviolet (UV) light is able to kill a wide array of micro-organisms that include, but not limited to, bacteria, viruses, spores, algae and protozoa, without having to chemically treat the object to be disinfected. One type of common UV bulb includes a quartz or glass casing that holds a vaporizable material, such as mercury, and also holds a stabilizing gas. The stabilizing gas may be one of the noble gases such as argon, neon, or xenon. An electrode positioned within the area sealed by the casing excites the stabilizing gas and vaporizable material. Ultraviolet light is emitted from a plasma field which is generated with the excited vaporizable material.

The ability of a UV light source to disinfect an object is primarily a function of exposure time and intensity of the exposure. For purposes of disinfecting or sanitizing a targeted object, it is therefore advantageous to use a source of UV light that consumes a minimum amount of power, yet produces an intense UV light output.

One of the more common types of UV light sources that are used as sanitizing/disinfecting agents are low pressure mercury lamps. Low pressure mercury lamps are generally cost effective in that their power requirements are low as compared to other types of UV light sources, yet low pressure mercury lamps also have a comparatively high UV output. One disadvantage with mercury lamps is that they are unable to adequately function in temperatures that fall outside optimal operating temperatures of the mercury lamps. UV light sources have been proven to be effective in sanitizing and disinfecting freezers/coolers used in the food handling industry; however, degradation in the performance of the UV light sources is experienced due to the colder temperatures that fall well below the optimal operating temperatures of the UV light sources. Low pressure mercury lamps are most efficient in producing ultraviolet light when the lamps are maintained at a temperature between about 80° to 90° F.

Therefore, it is apparent that a cost effective means is needed for providing UV disinfection/sanitization, particularly in those industries where ambient temperatures of objects to be sanitized are well below the optimal operating temperature ranges of a UV light source.

Also, there are circumstances when a UV light source may be subjected to temperatures that exceed optimal operating temperatures; thus, there is also a need to provide UV disinfection/sterilization in these conditions.

U.S. Patent Application Publication No. U.S. 2003/0001112 discloses a hermetically sealed ultraviolet light source in the form of an ultraviolet light bulb/lamp and a protective sleeve that surrounds the ultraviolet bulb. The sleeve helps to insulate the ultraviolet bulb which therefore helps to keep the bulb's plasma thermally stable.

U.S. Patent Application Publication No. 2003/00038247 discloses a watertight irradiation apparatus utilizing a microwave excited ultraviolet radiation generator that includes an electrodeless lamp. The UV radiation generator is enclosed within a watertight housing having an irradiation window allowing the UV rays to pass from the lamp to a target area.

While the prior art may suggest use of a covering to protect an otherwise exposed ultraviolet light source, a need still exists for providing an ultraviolet light source that may be selectively and controllably heated or cooled to optimize the output of the ultraviolet light source, regardless of the temperature at which the source is exposed to during use.

SUMMARY OF THE INVENTION

In accordance with the present invention, a heat controlled ultraviolet light apparatus is provided. The basic components of the apparatus include an ultraviolet light source, an ultraviolet transmissive cover placed over the light source, and a heating or cooling element placed within the cover to heat or cool the light source. The apparatus is placed at a desired distance from the object(s) to be disinfected/sanitized, and the ultraviolet light source is energized to deliver a desired amount of radiation in the form of ultraviolet light. The terms "disinfect" and "sanitize" as used herein are interchangeable terms, and collectively mean to free a targeted object from contaminants particularly in the form of living organisms such as the microorganisms mentioned above.

More specifically, the apparatus of the present invention includes a heating or cooling element that may be selectively controlled to provide the necessary amount of heating/cooling to maintain the ultraviolet light source at a desired temperature range thereby maximizing the efficiency of the UV light source in producing ultraviolet light. Preferably, the ultraviolet light source of the present invention can be categorized as a "hot UV" lamp, and more particularly, a low pressure mercury lamp that is most efficient in producing ultraviolet light when the lamp is maintained at a temperature between about 80–90° F. A heat sensor, such as a thermocouple or any other type of sensor, may be placed adjacent the ultraviolet light source to measure the temperature at which the light source operates. The heat sensor communicates with a control circuit which energizes the heating element at necessary intervals to maintain the light source within the optimal temperature range when the light source requires heating. For example, as temperature conditions may change, the heat sensor provides periodic inputs to the control circuit. The control circuit reacts accordingly to provide power to the heating element thereby maintaining the UV light source at the desired temperature range.

Alternatively, the heat sensor can be in the form of a temperature switch thereby eliminating the need for a separate control circuit, or at least reducing control circuit requirements.

If it is necessary to cool the UV light source, a cooling element can be used, such as a Peltier element, or a small cooling coil that may circulate a cooling medium therethrough. As necessary, a control circuit could be used to control the cooling element as well.

The cover not only helps to regulate temperature of the UV light source, but also helps to protect the UV light source from damage. The size and shape of the cover can be adapted for the specific use of the apparatus, as well as the type of ultraviolet light source used. The cover is larger than the bulb of the ultraviolet lamp thereby creating an airspace or gap between the cover and the bulb. Preferably, the heating/cooling element is placed in the gap/airspace between the cover and the lamp. A heating/cooling element having a higher output may allow the cover to be larger as the airspace between the cover and bulb would be more easily controlled, while a heating/cooling element with a lower output may require a smaller cover to allow the element to adequately control temperature in the airspace. One important aspect of the present invention is that the cover used be UV transmissive. Known materials which could be used that are UV transmissive include soft glass and quartz.

The UV light apparatus of the present invention can be used in even the most harsh environments, such as within an HVAC system, or a refrigeration unit wherein both environments would subject the apparatus to wide variances in temperature to include temperatures well below freezing.

With the apparatus of the present invention, disinfection of a targeted object can be accomplished in an energy efficient manner, thus reducing power requirements for the apparatus, as well as avoiding use of multiple apparatuses to achieve desired disinfectionss. Disinfection of the coils in systems such as an HVAC or refrigeration system also provides remedial and preventative maintenance benefits because the coils lose their ability to transfer heat if covered with microorganisms such as mold and algae. Motors and compressors must then work harder to compensate for the diminished coil performance. Thus, disinfection also helps to maintain proper operation of these systems to include saving power used by the systems.

Other features and advantages of the invention will become apparent from a review of the detailed description, taken in conjunction with the drawings, wherein like reference numbers refer to similar items throughout the figures.

BRIEF DESCRIPTION OF THE DRAWINGS

FIG. 1 is a perspective view of the ultraviolet light apparatus of the present invention, to include a schematic of circuitry supporting the apparatus;

FIG. 2 is an enlarged vertical section of the apparatus illustrating interior details;

FIG. 3 is another perspective view illustrating another embodiment;

DETAILED DESCRIPTION

Figure 4:
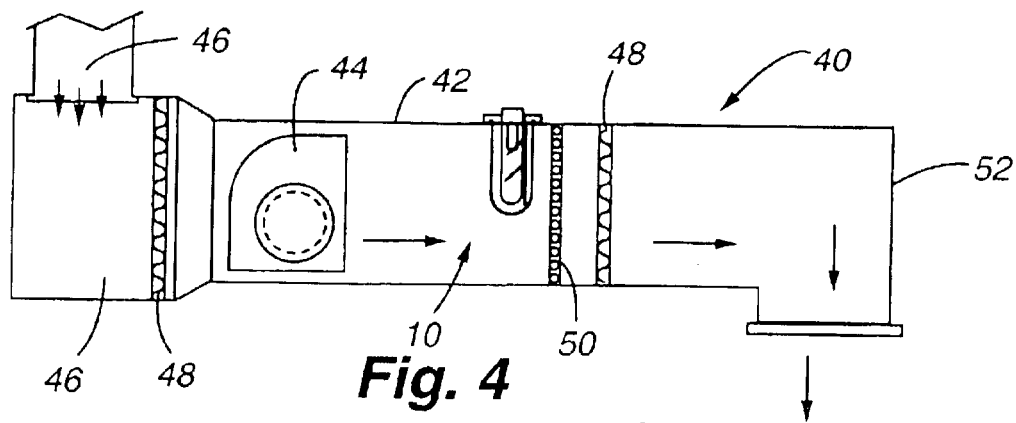
FIG. 4 is a schematic drawing of the apparatus of the present invention used within an HVAC system.

Referring first to FIG. 1, the heat controlled ultraviolet light apparatus 10 of the present invention is shown. The apparatus includes a UV transmissive cover 12, an ultraviolet lamp or bulb 14, and a heating/cooling element 18 that is placed in the gap or space between the bulb 14 and the cover 12. The particular type of ultraviolet bulb or lamp 14 shown includes one with a filament 16 which is used to excite a metal such as mercury housed in the lamp. One or more rare gases additionally fill the interior of the bulb so that a plasma field can be created, thus generating both visible and ultraviolet light. Although a particular type of ultraviolet lamp is shown, it shall be understood that the present invention can utilize any type of ultraviolet lamp. The bulb 14 may include an integral bulb base 20, which is most common in ultraviolet lamp constructions. As required, the bulb base may further include an internal ballast incorporated with base 20, or an external ballast 30 as shown.

Referring to FIG. 2, the apparatus of the present invention may further include a foundation or mount 21 which is used to secure the various elements of the apparatus. The mount 21 may be made from plastic, metal, or resin having a central opening therein sized to receive the bulb base 20. Preferably, the mount 21 is made of potting resin such that the mount 21 can be formed in a molding process to secure the elements of the apparatus. A slot or annular groove 22 can be formed on an upper surface of the mount 21 in order to receive a circumferential flange 24 formed on the cover 12. The slot 22 can be sized so that the flange 24 of the cover 12 frictionally engage the slot 22 thereby securing the cover 12 to the mount 21. Alternatively, the open end of the cover 12 may eliminate the flange 24, and the slot 22 can simply be sized with a width to frictionally engage the end of the cover 12. By this manner of attachment, the cover 12 can be sealed with respect to the bulb 14. Those skilled in the art can envision any number of additional ways in which the cover 12 may be secured to the mount 21. The heating/cooling element 18 has a lower end which is also received in the mount 21.

FIG. 2 further illustrates a temperature sensor 26 which may be mounted directly to the bulb 14, or may be secured to the mount 21 and positioned in the gap between the element 18 and the bulb 14. The sensor 26 includes a transmission line 27 which communicates with a control circuit 28. Sensor 26 acts as a temperature input to the control circuit. The element 18 also electrically connects with the control circuit 28 as by electrical line 29. The control circuit 28 would periodically energize/control the element 18 depending upon temperature inputs from sensor 26 to maintain the bulb 14 at a desired temperature range. A common power supply 32 can be used to power the ultraviolet lamp 14, as well as the control circuit 28 and heating element 18.

A preferred heating element is one made of a quartz material with a nichrome heating element etched on the quartz medium. The shape of the heating element is shown as being rectangular; however, any shape can be used, but preferably one which is of simple shape thereby minimizing manufacturing requirements. The heating element is also preferably sized to extend along the length of the lamp 14 thereby assuring a more uniform heating of the lamp.

A preferred cooling element may include a Peltier element, a small cooling coil that circulates a cooling medium therethrough, or any other acceptable cooling element that can fit in the gap between the lamp and the cover.

Referring now to FIG. 3, an alternate embodiment is shown. While FIG. 2 represents a cover 12 that may be sealed with respect to the lamp 14, FIG. 3 shows an arrangement wherein one portion of the lamp 14 is covered by the cover 12, yet other portions of the lamp 14 remain exposed. With the embodiment of FIG. 3 as used in some applications, it may be unnecessary to completely seal the cover with respect to the ultraviolet lamp. Thus, adequate heating/cooling of the lamp can take place if only a portion of the lamp remains covered during operation. For example, the apparatus of FIG. 3 could be used within a cooling unit that did not experience continued freezing temperatures, or the apparatus of FIG. 3 could be used to disinfect an object which might only occasionally be subject to cool temperatures. Structurally, the only modifications to the apparatus of FIG. 3 in comparison to the apparatus shown in FIG. 2 is that the cover does not completely cover the bulb and a plurality of supports 34 are used to attach the open end of the cover 12 to the mount 21.

In addition to providing clear open spaces around the lamp 14 as shown in FIG. 3, another method in which to provide a non-sealed cover would be to simply form a plurality of openings within the cover 12. Thus, a friction type engagement could still be used to attach the cover 12 to the mount 21, but the cover would not completely seal the lamp 14 because of the plurality of openings.

One acceptable material for the cover is a number 210 clear polished quartz of approximately 1/16th of an inch thickness. The cover is intended to be removable to facilitate periodic cleaning and replacement of not only the cover itself, but also of the heating element and/or UV lamp. Thus, in lieu of permanently affixing the base 20 of the lamp within the mount 21, a threaded attachment cold be used between the base 20 and the mount 21 thereby easing removal and replacement of the lamp 14.

FIG. 4 is a schematic diagram illustrating the apparatus 10 of the present invention used within a standard HVAC system 40. As shown, the HVAC system 40 may include a central duct 42, a fan 44, a return air duct 46, and an outlet duct 52. One or more filter elements 48 may be placed within the duct group as desired. Additionally, heating and/or cooling coils may traverse the central duct 42 thereby allowing heating or cooling of the air that passes through the HVAC system. The apparatus 10 is placed in close proximity to the cooling coils 50 to thereby sanitize/disinfect the cooling coils. As shown, the apparatus 10 can simply be mounted to the central duct 42 with the apparatus 10 extending a desired length into the duct space. Depending upon the size of the coils, the type and size of the ultraviolet lamp used, one or more apparatuses 10 can be used to disinfect sides of the cooling coils 50. Of course, the apparatus 10 can be placed at other locations with the HVAC system to provide sanitization benefits. As understood in the art, use of an ultraviolet light source also is effective in sanitizing the airstream itself.

Figure 5:
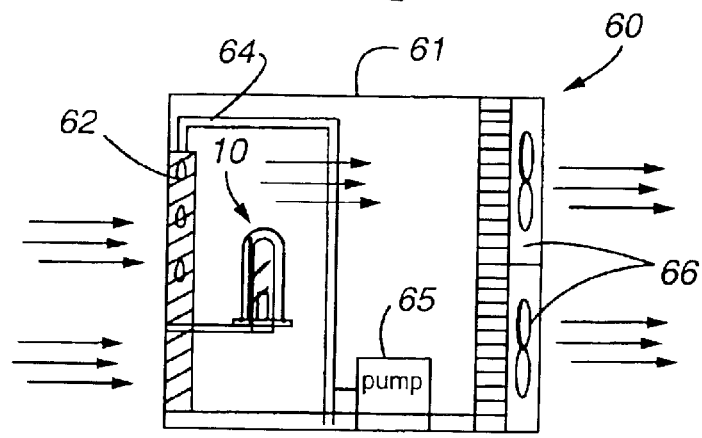
FIG. 5 is another schematic drawing of the apparatus of the present invention used within an evaporative cooler.

FIG. 5 illustrates use of the apparatus 10 within an evaporative cooling device 60. The evaporative cooling device 60 is generally characterized as including a housing 61, cooler batting 62 mounted at an inlet of the cooler, a liquid line 64 that provides a controlled drip of liquid over the batting, and a pump 65 to deliver the liquid. One or more fans 66 can be used to pull air through the cooler. Alternately, one or more fans 66 could be positioned upstream of the batting to push air through the device. The apparatus 10 is mounted in close proximity to the cooler batting 62 thereby providing disinfection of the same. One or more apparatuses 10 can be used and spaced from one another along the length of the batting 62 in order to achieve desired treatment.

Figure 6:
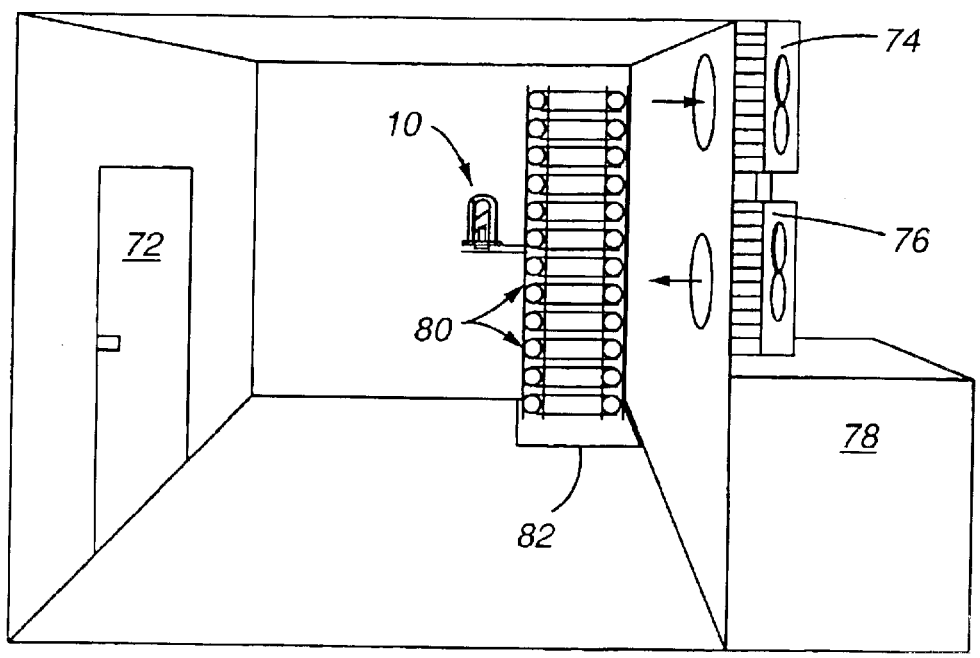
FIG. 6 is yet another schematic drawing illustrating the apparatus of the present invention used within a walk-in cooler/freezer.

FIG. 6 illustrates yet another example of use of the apparatus 10. FIG. 6 illustrates a common walk-in cooler or freezer. Accordingly, the cooler/freezer 70 may include an access door 72, which provides access to the temperature controlled space that may hold food or other perishables for storage. A common or generic refrigeration unit would include an inlet fan 76 for delivering cooled air, an exhaust fan 74 for removing air from the temperature controlled space, and a housing 78 to contain other elements of the refrigeration unit such as a compressor, expansion valve, etc. In order to optimize efficiency of the refrigeration unit, it is most common for the refrigeration unit to have its condenser coils 80 positioned within the temperature controlled space. Because heat transfer takes place from the condenser coils, the condenser coils themselves may be a source of microbial growth because they would normally be at a temperature higher than the surrounding air. Additionally, condensation may develop on the condenser coils 80, thereby necessitating the use of a drip pan 82 to catch the dripping liquid. The liquid within the drip pan 82 may also serve as a source for undesirable microbial growth. The apparatus 10 of the present invention would be mounted in close proximity to the coils 80. As necessary, more than one apparatus 10 may be used to optimally disinfect the coils 80 as well as to disinfect the drip pan 82 and the liquid that may be collected within the drip pan.

In all of the uses described in FIGS. 4, 5 and 6, the apparatus 10 of the present invention may be subject to temperatures well below the optimal temperature range of the ultraviolet lamp. Accordingly, the integral heating element allows selective and controllable heating of the UV lamp to thereby maximize the delivery of ultraviolet radiation to the targeted objects to be disinfected. Although low pressure mercury lamps may have an optimal operating temperature range between about 80–90 degrees F, the apparatus of the present invention is well suited to provide necessary heat for lamps that may operate at many other temperature ranges.

In addition to the apparatus of the present invention, the present invention also includes methods of sanitizing various objects to include coils of a refrigeration unit, and coils of an HVAC system/evaporative cooling device. Although these three specific methods have been described and claimed herein, the apparatus of the present invention can be used in many other applications as well.

The apparatus and methods of the present invention have been described with respect to preferred embodiments; however, it shall be understood that various other changes and modifications can be made within the spirit and scope of the present invention as claimed.

What is claimed is:

1. A heat controlled ultraviolet light apparatus comprising:

an ultraviolet light source;

an ultraviolet transmissive cover placed over said light source; and a heating element placed within said cover and adjacent said ultraviolet light source to selectively heat said ultraviolet light source thereby maintaining the light source within an optimum temperature range.

2. An apparatus, as claimed in claim 1, further including:

a heat sensor placed adjacent to said light source; and a control circuit communicating with said heat sensor to selectively control output of heat from said heating element by signals received from said heat sensor indicating the temperature around said ultraviolet light source.

3. An apparatus, as claimed in claim 1, further including:

a heat switch placed adjacent to said light source to sense temperature around said ultraviolet light source and to selectively energize said heating element.

4. An apparatus, as claimed in claim 1, wherein:

said cover is made from quartz.

5. An apparatus, as claimed in claim 1, wherein:
said cover is made from glass.

6. An apparatus, as claimed in claim 1, wherein:
said heating element includes a quartz medium and a nichrome element etched on said quartz medium.

7. An apparatus, as claimed in claim 1, wherein:
said cover is sealed with respect to said ultraviolet light source.

8. An apparatus, as claimed in claim 1, wherein:
said cover surrounds a first portion of said ultraviolet light source and a second portion of said ultraviolet light source remains exposed.

9. An apparatus, as claimed in claim 1, wherein:
said apparatus further includes a mount for securing said ultraviolet light source, said cover, and said heating element.

10. An apparatus, as claimed in claim 9, wherein:
said cover has a circumferential edge received in said mount.

11. A heat controlled ultraviolet light apparatus comprising:
an ultraviolet light source;
an ultraviolet transmissive cover placed over said ultraviolet light source; and
means for heating said ultraviolet light source to maintain said ultraviolet light source within a desired temperature range said means for heating being placed within said cover.

12. An apparatus, as claimed in claim 11, wherein:
said means for heating includes a heating element, and a control circuit communicating with said heating element to thereby monitor temperature around said ultraviolet light source and to activate said heating element to maintain said ultraviolet light source within the desired temperature range.

13. An apparatus, as claimed in claim 11, wherein:
said cover is made from quartz.

14. An apparatus, as claimed in claim 11, wherein:
said cover is made from glass.

15. An apparatus, as claimed in claim 11, wherein:
said means for heating includes a quartz medium and a nichrome element etched on said quartz medium.

16. An apparatus, as claimed in claim 11, wherein:
said cover is sealed with respect to said ultraviolet light source.

17. An apparatus, as claimed in claim 11, wherein:
said cover surrounds a first portion of said ultraviolet light source and a second portion of said ultraviolet light source remains exposed.

18. An apparatus, as claimed in claim 11, wherein:
said apparatus further includes a mount for securing said ultraviolet light source, said cover, and said means for heating.

19. An apparatus, as claimed in claim 18, wherein:
said cover has a circumferential edge received in said mount.

20. An apparatus, as claimed in claim 11, further including:
a heat switch placed adjacent to said light source to sense temperature around said ultraviolet light source and to selectively energize said means for heating.

21. A heat controlled ultraviolet light apparatus comprising:
a mount;
an ultraviolet light source secured to said mount, said ultraviolet light source comprising an ultraviolet light producing bulb;
an ultraviolet transmissive cover placed over said ultraviolet light source and secured to said mount;
a heating element placed between said cover and said ultraviolet light source; and
means communicating with said heating element for controlling said heating element to produce an amount of heat to maintain said ultraviolet light source within a desired temperature range thereby maximizing the efficiency of ultraviolet light source to produce ultraviolet light.

22. An apparatus, as claimed in claim 21, wherein:
said means for controlling includes a heat sensor placed adjacent to said ultraviolet light source, and a control circuit communicating with said heat sensor.

23. An apparatus, as claimed in claim 21, wherein:
said heating element includes a quartz medium and a nichrome element etched on said quartz medium.

24. An apparatus, as claimed in claim 21, wherein:
said cover is sealed with respect to said ultraviolet light source.

25. An apparatus, as claimed in claim 21, wherein:
said mount is formed by molding, and is made from the group consisting of thermoplastics, metals, and resins.

26. An apparatus, as claimed in claim 21, wherein:
said cover surrounds a first portion of said ultraviolet light source and a second portion of said ultraviolet light source remains exposed.

27. An apparatus, as claimed in claim 21, wherein;
said means for controlling includes a temperature switch.

28. A method of sanitizing coils of a refrigeration unit, said method comprising the steps of:
providing a refrigeration unit including condenser coils placed within an airspace to be cooled by said refrigeration unit;
providing an ultraviolet light source;
placing a heating element in close proximity to said ultraviolet light source;
covering the ultraviolet light source with a cover thereby making a heat controlled ultraviolet light source said heating element being placed within said cover;
positioning the UV light source in close proximity to the condenser coils;
providing heat to said ultraviolet light source by said heating element to maintain said ultraviolet light source at an optimal temperature range thereby maximizing the efficiency of said ultraviolet light source in producing ultraviolet light; and
exposing said condenser coils to ultraviolet radiation produced by said ultraviolet light source to achieve desired sanitization of said condenser coils.

29. A method of sanitizing heating and/or cooling coils of an HVAC system, said method comprising the steps of:
providing an HVAC system including heating and/or cooling coils that traverse across a duct of said HVAC system;
providing an ultraviolet light source;
placing a heating element in close proximity to said ultraviolet light source;

covering the ultraviolet light source with a cover thereby making a heat controlled ultraviolet light source said heating element being placed within said cover;

positioning the UV light source in close proximity to the coils;

providing heat to said ultraviolet light source by said heating element to maintain said ultraviolet light source at an optimal temperature range thereby maximizing the efficiency of said ultraviolet light source in producing ultraviolet light; and exposing said coils to ultraviolet radiation produced by said ultraviolet light source to achieve desired sanitization of the coils.

30. A heat controlled ultraviolet light apparatus comprising:

an ultraviolet light source;

an ultraviolet transmissive cover placed over said light source; and a cooling element placed within said cover and adjacent said ultraviolet light source to selectively cool said ultraviolet light source thereby maintaining the light source within an optimum temperature range.

31. A heat controlled ultraviolet light apparatus comprising:

an ultraviolet light source;

an ultraviolet transmissive cover placed over said ultraviolet light source; and means for cooling said ultraviolet light source to maintain said ultraviolet light source within a desired temperature range said means for cooling being placed within said cover.

32. A heat controlled ultraviolet light apparatus comprising:

a mount;

an ultraviolet light source secured to said mount, said ultraviolet light source comprising an ultraviolet light producing bulb;

an ultraviolet transmissive cover placed over said ultraviolet light source and secured to said mount;

a cooling element placed between said cover and said ultraviolet light source; and means communicating with said heating element for controlling said cooling element to produce an amount of cooling to maintain said ultraviolet light source within a desired temperature range thereby maximizing the efficiency of ultraviolet light source to produce ultraviolet light.

\* \* \* \* \*

UNITED STATES PATENT AND TRADEMARK OFFICE
CERTIFICATE OF CORRECTION

PATENT NO. : 6,924,495 B1
DATED : August 2, 2005
INVENTOR(S) : Brickley

It is certified that error appears in the above-identified patent and that said Letters Patent is hereby corrected as shown below:

Column 7,
Line 30, please insert a comma -- , -- immediately after "range.".

Column 8,
Line 47, please insert a comma -- , -- immediately after "source.".

Column 9,
Line 2, please insert a comma -- , -- immediately after "source.".

Column 10,
Line 6, please insert a comma -- , -- immediately after "range.".

Signed and Sealed this

Eleventh Day of October, 2005

JON W. DUDAS
*Director of the United States Patent and Trademark Office*